United States Patent [19]

Chartier et al.

[11] Patent Number: 6,110,735

[45] Date of Patent: *Aug. 29, 2000

[54] METHOD FOR THE PREPARATION OF A VIRAL VECTOR BY INTERMOLECULAR HOMOLOGOUS RECOMBINATION

[75] Inventors: Cécile Chartier; Eric Degryse, both of Strasbourg, France

[73] Assignee: Transgene, S.A., Strasbourg, France

[*] Notice: This patent issued on a continued prosecution application filed under 37 CFR 1.53(d), and is subject to the twenty year patent term provisions of 35 U.S.C. 154(a)(2).

[21] Appl. No.: 08/682,794

[22] PCT Filed: Dec. 1, 1995

[86] PCT No.: PCT/FR95/01590

§ 371 Date: Aug. 1, 1996

§ 102(e) Date: Aug. 1, 1996

[87] PCT Pub. No.: WO96/17070

PCT Pub. Date: Jun. 6, 1996

[30] Foreign Application Priority Data

Dec. 1, 1994 [FR] France .................................. 94 14470

[51] Int. Cl.$^7$ ........................ A61K 39/235; C07H 21/04; C07K 14/075; C12N 1/21

[52] U.S. Cl. .................................. 435/320.1; 435/252.1; 435/252.3; 435/252.33; 435/252.8; 435/235.1; 435/172.3; 424/233.1; 514/44; 530/350

[58] Field of Search ............................. 435/320.1, 252.8, 435/235.1, 252.3, 252.33, 172.3, 252.1; 424/233.1; 514/44; 530/350

[56] References Cited

U.S. PATENT DOCUMENTS 5,582,362  12/1996  Wilson et al. .

FOREIGN PATENT DOCUMENTS

WO91/11525  8/1991  WIPO .
95/03400    2/1995  WIPO .

OTHER PUBLICATIONS

Proceedings of the National Academy of Sciences, USA, vol. 91, No. 13, 1994 Washington US, pp. 6186–6190, G. Ketner et al, "Efficient Manipulation of the Human Adenovirus Genome as an Efficious Yeast Artificial Chromosome Clone".

Journal of Biotechnology, vol. 39, No. 2, 1995 Amsterdam NL, E. Degryse, "Evaluation of *Escherichia Coli* recBC sbcBC Mutants for Cloning by Recombination in Vivo".

Virus Research, vol. 28, No. 2, 1993, pp. 153–170, J. Schorr & Doerfler, "Non–homologous Recombination Between Adenovirus and AcNPV DNA Fragments in Cell–free Extracts from Insect *Spodoptera Frugiperda* Nuclei".

Science, vol. 196, No. 4286, 1977 Lancaster, PA US, M. Perricaudet et al, "Excision and Recombination of Adenovirus DNA Fragments in *Escherichia Coli*".

Nucleic Acids Research, vol. 21, No. 4, 1993, pp. 817–821, A.C. Boyd, "Turbo Cloning: A Fast Efficient Method for Cloning PCR Products and Other Blunt–Ended DNA Fragments Into Plasmids".

Yeast, vol. 11, No. 7, 1995, pp. 629–640, Degryse et al, "In Vivo Cloning by Homologous Recombination in Yeast Using a Two–Plasmid–Based System".

Journal of Molecular Biology, vol. 227, No. 1, 1992, pp. 72–80 Luisi–De Luca, & Kolodner, "Effects of Terminal Non–homology on Intromolecular Recombination of Linear Plasmid Substrates in *Escherichia Coli*".

Proceedings of the National Academy of Sciences of USA, vol. 90, No. 15, Sep. 1993 Washington US, pp. 7356–7360, Tatzelt et al, "Fractionated Nuclear Extracts from Hamster Cells Catalyze Cell–Free Recombination at Selective Sequences Between Adenovirus DNA and a Hamster Pre-insertion Site".

Gene Therapy, vol. 2, No. 4, Jun. 1995, pp. 263–268, Imler et al, "An Efficient Procedure to Select and Recover Recombinant Adenovirus Vectors".

Nucleic Acids Research, vol. 21, No. 15, Jul. 25, 1993 Oxford, GB, pp. 3601–3602, P. Bubeck et al, "Rapid Cloning by Homologous Recombination In Vivo".

Methods: A Companion to Methods in Enzymology, vol. 5, 1993, pp. 161–175, F. Spencer et al, "Targeted Recombination–Based Cloning and manipulation of Large DNA Segments in Yeast".

Lewin, Science 237, 1987, p1570.

Hamir et al. Vet Pathol 29(6). Nov. 1992, p509–513.

Report and Recommendations of the Panel to Access the NIH Investment in Research on Gene Therapy, Dec. 7, 1995.

Coglan, New Scientist Nov. 25, 1995, p 14–15.

Jelinek et al. J Virol 66(7) Jul. 1992, p 4117–4125.

Yamamoto et al. Mol Gen Genet 234(1), 1992, p 1–13.

Coglan A. New Scientist, Nov. 25, 1995, p. 14–15.

Shenk, T. Adenoviridae: The Vimses and Their Replication. *Fields Virology*, Fields et al., Ed. Chap 67, p. 2111–2148, 1996.

*Primary Examiner*—Phuong T. Bui
*Attorney, Agent, or Firm*—Burns, Doane, Swecker & Mathis, L.L.P.

[57] ABSTRACT

A recombinant adenoviral vector containing an exogenous DNA sequence insertion is prepared in a prokaryotic cell using homologous intermolecular recombination. The exogenous DNA sequence codes for a polypeptide of therapeutic interest for applications in gene therapy. The adenoviral vector may lack all or part of at least one region essential for replication.

18 Claims, 4 Drawing Sheets

Figure 4

METHOD FOR THE PREPARATION OF A VIRAL VECTOR BY INTERMOLECULAR HOMOLOGOUS RECOMBINATION

The present invention relates to a method for preparing a viral vector in vitro in a prokaryotic cell and to its application for producing an infectious viral particle intended for therapeutic use, and especially for use in gene therapy.

The possibility of treating human diseases by gene therapy has changed in a few years from the stage of theoretical considerations to that of clinical applications. The first protocol applied to man was initiated in the US in September 1990 on a patient who was genetically immunodeficient as a result of a mutation affecting the gene coding for adenine deaminase (ADA). The relative success of this first experiment encouraged the development of new gene therapy protocols for various genetic or acquired diseases (infectious diseases, and viral diseases in particular, such as AIDS, or cancers). The large majority of the protocols described hitherto employ viral vectors to transfer the therapeutic gene to the cells to be treated and to express it therein.

To date, retroviral vectors are among the ones most widely used on account of the simplicity of their genome. However, apart from their restricted capacity for cloning, they present two major drawbacks which limit their systematic use: on the one hand they chiefly infect dividing cells, and on the other hand, as a result of their integration at random in the genome of the host cell, the risk of insertional mutagenesis is not insignificant. For this reason, many scientific teams have endeavored to develop other types of vector, among which those originating from adenoviruses, adeno-associated viruses (AAV), poxviruses and herpesviruses may be mentioned. Generally speaking, their organization and their infection cycle are amply described in the literature available to a person skilled in the art.

Figure 1:
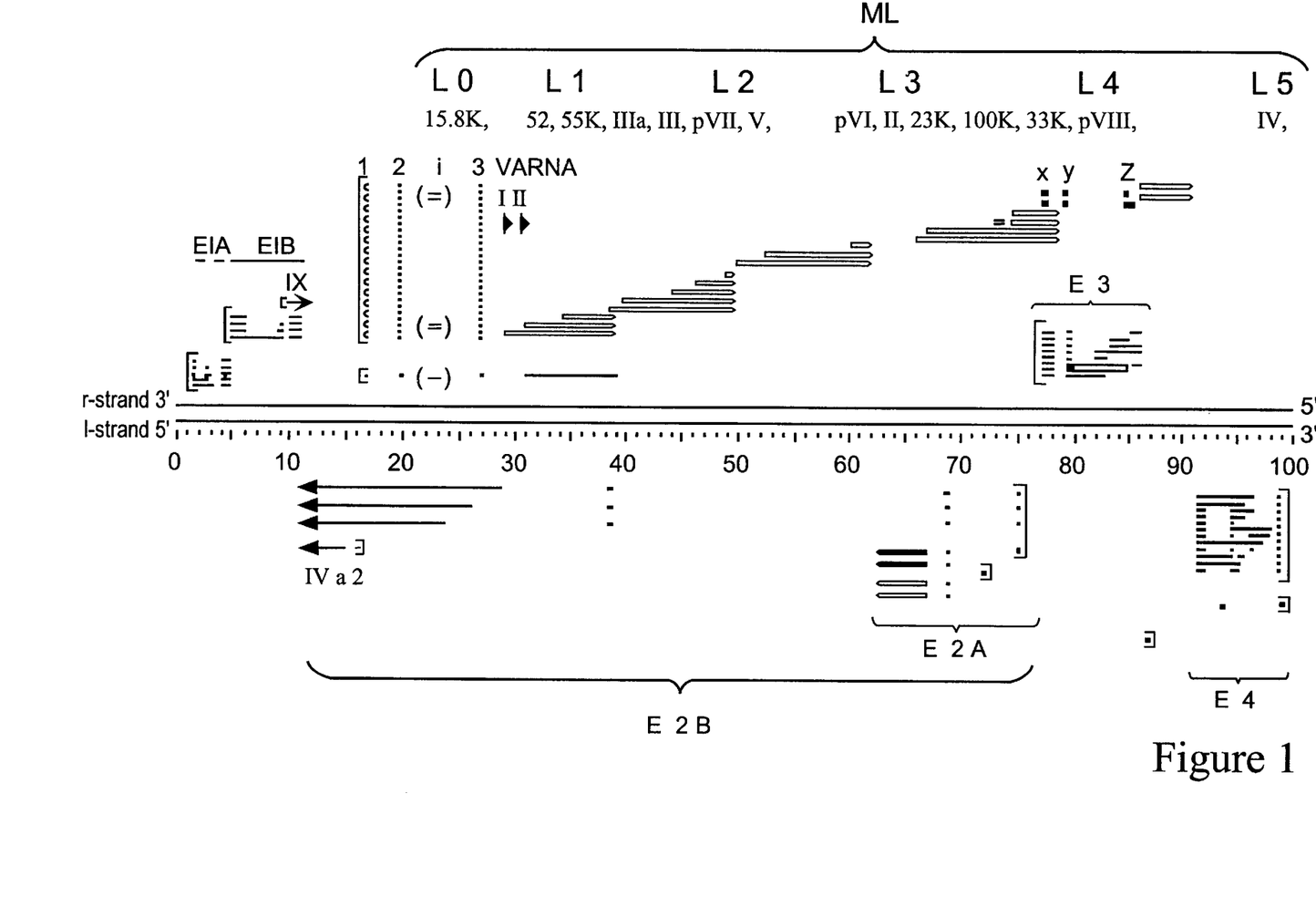
FIG. 1 is a diagrammatic representation of the human adenovirus type 5 genome (shown in arbitrary units from 0 to 100), indicating the location of the different genes.

In this connection, the use of adenoviral vectors has been seen to be a promising alternative. Adenoviruses have been demonstrated in many animal species, have a broad host range, have little pathogenicity and do not present the drawbacks associated with retroviruses since they replicate in resting cells and are nonintegrative. As a guide, their genome consists of a linear, double-stranded DNA molecule of approximately 36 kb carrying more than about thirty genes, both early genes necessary for viral replication (E1 to E4) and late structural genes (L1 to L5) (see FIG. 1).

Generally speaking, the adenoviral vectors are obtained by deletion of at least one portion of the viral genes (in particular of the E1 region essential for viral replication), which are replaced by the therapeutic genes. Consequently, they are propagated in a cell line, termed complementation line, which supplies in trans the deleted viral functions to generate a viral vector particle which is defective for replication but capable of infecting a host cell. The line 293, established from human embryonic kidney cells, which complements adenoviruses that are defective for the E1 function (Graham et al., 1977, J. Gen. Virol., 36, 59–72), is commonly used.

The techniques of preparation of adenoviral vectors are amply described in the literature (see, in particular, Graham and Prevec, Methods in Molecular Biology, Vol. 7; Gene Transfer and Expression Protocols; Ed: E. J. Murray, 1991, The Human Press Inc., Clinton, N.J.). One of the methods most often employed consists in generating the recombinant adenoviral vector in complementation cells transfected with a bacterial plasmid carrying the gene of interest subcloned within its adenoviral insertion region and the adenoviral genome. Generally, the latter is cleaved with a suitable restriction enzyme so as to reduce the infectivity of the parent viral DNA and to increase the efficiency of isolation of the recombinant adenoviruses. However, a substantial background of infectious viral particles of parenteral origin is nevertheless observed, which necessitates an especially arduous task of analysis of the plaques obtained (arduous from a time and cost standpoint, since each plaque has to be amplified and analyzed individually). This is problematical when the parent virus displays a selective advantage over the recombinant adenovirus, for example when the latter replicates more slowly than the parent virus as a result of the insertion of a large-sized gene of interest (factor VIII, dystrophin), reducing proportionately the probability of obtaining it.

Ligation between two DNA fragments generated by the standard techniques of molecular biology and carrying, respectively, the 5' and 3' portions of the recombinant adenoviral vector may also be employed. Transfection of the ligation mixture into the complementation cells makes it possible in theory to encapsidate the genome of the recombinant adenovirus to form an infectious particle. This technology is of low efficiency and its application limited by the restricted number of suitable and unique restriction sites.

Figure 2:
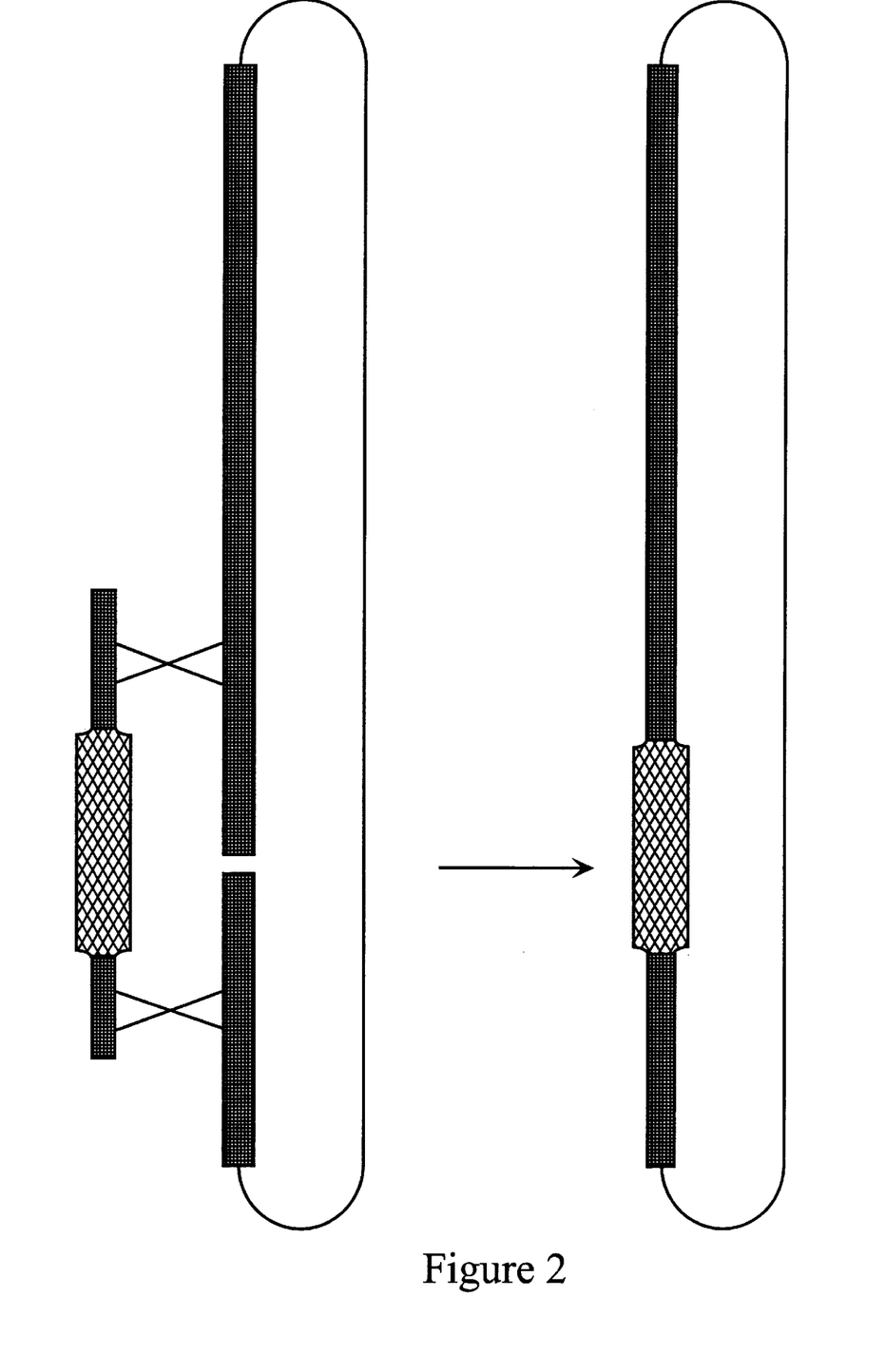
FIG. 2 illustrates a method of intermolecular recombination between two DNA fragments. The plasmid sequences are represented by a thin line, the viral sequences by a thick line and the exogenous sequence by a shaded box.

It has now been shown to be possible to generate a recombinant adenoviral vector in *Escherichia coli* (*E. coli*) by intermolecular homologous recombination between a plasmid containing the genome of a type 5 adenovirus and an insert carrying an exogenous DNA sequence surrounded by adenoviral sequences A and B (FIG. 2). This method leads to the replacement in the adenoviral genome of the targeted region located between A and B by the exogenous sequence. Transfection of the recombinant adenoviral vector thus generated into an appropriate complementation line gives rise to an infectious viral particle which may be used without a prior purification step to infect a host cell. The background (contamination with parent viral particles) is reduced or even abolished. In addition, it was found, surprisingly, that the use of *E. coli* recBC sbcBC strains is especially advantageous for promoting intermolecular recombination between any two DNA fragments.

The method of the present invention is based on exploitation of the endogenous enzymatic activities of the prokaryotic cells involved in homologous recombination. This intermolecular recombination technique had already been described for the cloning of small inserts into bacterial vectors (Bubeck et al., 1993, Nucleic Acids Research, 21, 3601–3602) or for generating hybrid genes by intramolecular recombination (Calogero et al., 1992, FEMS Microbiology Letters, 97, 41–44; Caramori et al., 1991, Gene, 98, 37–44). However, this recombination technology had never been employed in prokaryotic cells to generate infectious viral vectors (capable of being encapsidated into infectious viral particles).

The method of the invention has the advantage over the previous techniques of being rapid and especially efficient, and of requiring only a small number of manipulations in vitro. Furthermore, it may be employed with DNA fragments generated by PCR (polymerase chain reaction), thereby avoiding the steps of subcloning of the exogenous DNA sequence into the insertion region of the viral genome. Lastly, it provides an advantageous solution to the problem of background which is clearly identified in the literature. Consequently, it proves especially efficacious for vectors originating from large-sized viruses or viruses into which the insertion of a large-sized exogenous DNA sequence is envisaged.

Accordingly, the subject of the present invention is a method for preparing, in a prokaryotic cell, a recombinant viral vector derived from a parent virus into the genome of which an exogenous DNA sequence is inserted, by intermolecular recombination between (i) a first DNA fragment comprising all or part of said genome of the parent virus and (ii) a second DNA fragment comprising said exogenous DNA sequence surrounded by flanking sequences A and B which are homologous to (i).

For the purposes of the present invention, a recombinant viral vector is obtained from a parent virus modified so as to carry at a suitable site of the viral genome and to express an exogenous DNA sequence. The parent viruses capable of being used in the context of the invention are, for example, alphaviruses, retroviruses, poxviruses, and in particular vaccinia or canarypox virus, herpesviruses, adeno-associated viruses (AAV) and most especially adenoviruses.

In this connection, the choice of parent adenovirus is very wide. It can be an adenovirus of human, canine, avian, bovine, murine, ovine, porcine or simian origin, or alternatively a hybrid adenovirus comprising adenoviral genome fragments of different origins. Very special preference will be given to a serotype C adenovirus of human origin and preferably a type 2 or 5 adenovirus, or alternatively to an adenovirus of animal origin of the CAV-1 or CAV-2 (canine), DAV (avian) or alternatively BAd (bovine) type. These viruses and their genome are described in the literature (see, for example, Zakharchuk et al., 1993, Arch. Virol., 128, 171–176; Spibey and Cavanagh, 1989, J. Gen. Virol., 70, 165–172; Jouvenne et al., 1987, Gene, 60, 21–28; Mittal et al., 1995, J. Gen. Virol., 76, 93–102).

The objective of a method according to the invention is to prepare a recombinant viral vector for the transfer of an exogenous DNA sequence to a host cell and its expression therein. "Exogenous DNA sequence" is understood to mean a nucleic acid which comprises coding sequences and regulatory sequences permitting the expression of said coding sequences, and in which the coding sequences are sequences which are not normally present in the genome of a parent virus employed in the present invention or, if they are present, are in a different genomic context. In the context of the invention, the exogenous DNA sequence may be composed of one or more genes. The regulatory sequences may be of any origin.

Preferably, the exogenous DNA sequence can code for an antisense RNA and/or an mRNA which will then be translated into a protein of interest. It may be of the genomic type, of the complementary DNA (cDNA) type or of mixed type (minigene, in which at least one intron is deleted). It may code for a mature protein, a precursor of a mature protein, in particular a precursor intended to be secreted and, as a result, comprising a signal peptide, a chimeric protein originating from the fusion of sequences of diverse origins or a mutant of a natural protein displaying improved or modified biological properties. Such a mutant may be obtained by mutation, deletion, substitution and/or addition of one or more nucleotide(s) of the gene coding for the natural protein.

In the context of the present invention, it can be advantageous to use:

the genes coding for cytokines or lymphokines, such as interferons α, β and γ, interleukins, and in particular IL-2, IL-6 or IL-10, tumor necrosis factors (TNF) and colony stimulating factors (CSF);

the genes coding for cell receptors, such as the receptors recognized by pathogenic organisms (viruses, bacteria or parasites), preferably by the HIV virus (human immunodeficiency virus), or ligands for cell receptors;

the genes coding for growth hormones (HGF);

the genes coding for coagulation factors, such as factor VIII and factor IX;

the gene coding for dystrophin or minidystrophin;

the gene coding for insulin;

the genes coding for polypeptides participating directly or indirectly in cellular ion channels, such as the CFTR (cystic fibrosis transmembrane conductance regulator) protein;

the genes coding for antisense RNAs or proteins capable of inhibiting the activity of a protein produced by a pathogenic gene present in the genome of a pathogenic organism, or by a cellular gene whose expression is deregulated, for example an oncogene;

the genes coding for a protease inhibitor such as $\alpha_1$-antitrypsin or an inhibitor of a viral protease;

the genes coding for variants of pathogenic proteins which have been mutated in such a way as to impair their biological function, such as, for example, trans-dominant variants of the HIV virus TAT protein which are capable of competing with the natural protein for binding to the target sequence, thereby preventing the replication of HIV;

the genes coding for antigenic epitopes so as to increase the immunity of the host cell;

the genes coding for polypeptides having anticancer properties, and in particular tumor suppressors such as the p53 protein;

the genes coding for proteins of the major histocompatibility complex classes I and II, as well as the genes coding for the proteins that regulate the expression of these genes;

the genes coding for cellular enzymes or those produced by pathogenic organisms; and suicide genes. The HSV-1 TK gene may be mentioned more especially. The viral TK enzyme displays a markedly greater affinity than the cellular TK enzyme for certain nucleoside analogs (such as acyclovir or ganciclovir). It converts them to monophosphated molecules, which are themselves convertible by the cellular enzymes to nucleotide precursors, which are toxic. These nucleotide analogs can be incorporated in DNA molecules in the process of synthesis, hence mainly in the DNA of cells undergoing replication. This incorporation enables dividing cells such as cancer cells to be destroyed specifically.

the genes coding for an antibody, an antibody fragment or an immunotoxin.

reporter genes such as the LacZ gene coding for β-galactosidase, or the luciferase gene.

This list is not limiting, and other genes may naturally be employed as well.

Moreover, an exogenous DNA sequence employed in the present invention may comprise, in addition, a nontherapeutic gene, for example a gene coding for a selectable marker enabling the transfected host cells to be selected or identified. There may be mentioned the neo gene (coding for neomycin phosphotransferase) conferring resistance to the antibiotic G418, the dhfr (dihydrofolate reductase) gene, the CAT (chloramphenicol acetyltransferase) gene, the pac (puromycin acetyltransferase) gene or alternatively the gpt (xanthine:guanine phosphoribosyltransferase) gene.

Naturally, a gene employed in the present invention may be placed under the control of elements suitable for its expression in a host cell. "Suitable elements" are understood to mean the set of elements necessary for its transcription into RNA (antisense RNA or mRNA) and for the translation of an mRNA into protein. Among elements necessary for transcription, the promoter assumes special importance. The latter can be a constitutive promoter or a regulable promoter, and it may be isolated from any gene of eukaryotic or even of viral origin. Alternatively, it can be the natural promoter of the gene in question. Generally speaking, a promoter employed in the present invention may be modified so as to contain regulatory sequences. As examples of tissue-specific promoters, there may be mentioned those of the immunoglobulin genes when it is sought to target the expression into lymphocytic host cells, and of the $\alpha_1$-antitrypsin gene for a liver-specific expression. The constitutive promoters of the HSV-1 TK (herpesvirus type 1 thymidine kinase) and of the murine or human PGK (phosphoglycerate kinase) gene, the SV40 (simian virus 40) early promoter, a retroviral LTR or alternatively the adenoviral MLP promoter, in particular of human adenovirus type 2, may also be mentioned.

The method according to the invention employs an intermolecular homologous recombination mechanism. Generally speaking, it consists of the exchange of homologous sequences between two DNA fragments. These sequences may be identical or substantially homologous. In other words, the degree of homology of the sequences A and B with the corresponding portion of the first DNA fragment may be variable, but must be sufficient to permit intermolecular recombination. For the purposes of the present invention, it is preferable for it to be greater than 70%, advantageously greater than 80%, preferably greater than 90%, and as an absolute preference in the region of 100%. Furthermore, a short region of homology may be sufficient (at least 10 consecutive nucleotides in common between the sequences A and B and their homologous sequences in the first DNA fragment). In the context of the present invention, the length of the sequences A and B is preferably between 10 bp and 10 kb, advantageously 20 bp and 5 kb, preferably 30 bp and 2 kb, and as an absolute preference 40 bp and 1 kb.

According to an advantageous embodiment, a method according to the invention leads to the replacement of the genetic material localized between the sequences of the first DNA fragment which are homologous to the sequences A and B by the exogenous sequence. This intermolecular exchange enables a circular recombinant viral vector to be generated in the form of a prokaryotic vector (plasmid, cosmid or phage) permitting its manipulation and/or its propagation in the prokaryotic cell. An embodiment of the mechanism employed in the context of the present invention is illustrated in FIG. 2.

Although the insertion region of the exogenous sequence may be located in any position of the viral genome, it is preferable to avoid the regions acting in cis necessary for replication. These regions comprise, in particular, the 5' and 3' LTRs as well as the encapsidation signal in the case of retroviruses, and the 5' and 3' ITRs and the encapsidation region as regards adenoviruses. It would appear that the insertion region may be directed into a variety of positions in accordance with the chosen homologous sequences A and B.

As stated above, the first DNA fragment comprises all or part of the genome of the parent virus employed in the context of the invention. This may be the genome of a wild-type virus or the genome of a virus derived therefrom, modified by deletion, addition and/or substitution of one or more nucleotides. In particular, one or more genes may be wholly or partially deleted from the genome in question.

The first DNA fragment is preferably included in a conventional vector. The choice of the latter is very wide, but pBR322, p polyII or alternatively p polyIII*I (Lathe et al., 1987, Gene, 57, 193–201) may be mentioned more especially. According to an advantageous embodiment of the method according to the invention, the first DNA fragment is preferably linearized in the region in which the targeting of the insertion is envisaged. In particular, it may be cleaved with one or more restriction enzymes whose sites are localized between the sequences of the first DNA fragment which are homologous to the sequences A and B, but also within these latter, although this embodiment is not preferred. The choice of restriction sites to be used according to the parent virus adopted is within the capacity of a person skilled in the art. Advantageously, it will be preferable to use sites which are not strongly represented in the first DNA fragment, and especially unique sites. Moreover, such sites may also be created by the standard techniques of directed mutagenesis.

The second DNA fragment employed in the present invention carries, in particular, the exogenous DNA sequence surrounded by the sequences A and B involved in the intermolecular recombination. It is preferable to employ a linear DNA fragment. It may be generated by PCR, excised from any vector or produced synthetically or by any conventional method in the field of the art. As an example, a second DNA fragment employed in the context of the present invention may be obtained by amplification of the exogenous DNA sequence from a vector of the prior art or from a genomic library or from an appropriate cDNA using suitable primers equipped at their 5' ends with the sequences A and B. In addition, a second DNA fragment may also comprise plasmid sequences at its 5' and 3' ends, which may optionally be used by way of sequences A and B provided they are homologous to the plasmid sequences contained in the first DNA fragment.

In accordance with the objectives pursued by the present invention, a method according to the invention is carried out for the preparation of a recombinant viral vector which is defective for replication. This term denotes a vector incapable of completing an autonomous infectious cycle in a host cell. Generally, the genome of these defective vectors lacks one or more genes essential for replication, early genes and/or late genes. They may be wholly or partially deleted or rendered nonfunctional by mutation (addition, deletion and/or substitution of one or more nucleotides). In this connection, a method according to the invention can enable a recombinant adenoviral vector lacking all or part of the E1, E2, E3 and/or E4 regions to be prepared.

By way of illustration, the following embodiments may be mentioned. When the intention is to prepare, in a prokaryotic cell, a recombinant adenoviral vector derived from a type 5 human adenovirus (Ad5) in which the insertion of an exogenous DNA sequence in place of the E1 region is envisaged, it is possible to employ (i) a vector containing the Ad5 genome cleaved with the enzyme ClaI (restriction site located at position 918 of the Ad5 genome, as disclosed in the Genebank databank under the reference M73260), and (ii) a DNA fragment comprising a sequence A homologous to the adenoviral encapsidation region, the exogenous DNA sequence followed by a sequence B homologous to the sequence coding for the pIX protein. Moreover, the use of a vector carrying the adenoviral genome cleaved with the enzyme SpeI (position 27082 of the Ad5 genome) and of a DNA fragment comprising a sequence A homologous to the 5' end of the E2 region, the exogenous DNA sequence and a sequence B homologous to the 3' end of the E4 region will enable a recombinant adenoviral vector to be prepared in which the exogenous DNA sequence is inserted in place of the E3 region. Naturally, these particular embodiments are mentioned only as examples. Lastly, the method according to the invention may be used to introduce deletions, mutations and/or substitutions into a particular region of a viral genome.

The present invention proves especially advantageous when the intention is to prepare a recombinant viral vector of at least 20 kb, and as an absolute preference of at least 30 kb, and more especially in the case of a vector having a genome whose length is from 80 to 120% of that of the genome of the corresponding wildtype virus, in particular from 90 to 110% and preferably from 95 to 105%.

According to another embodiment, a method according to the invention may also be employed to insert at least two DNA fragments within the viral genome, by intermolecular recombination between (i) a first DNA fragment comprising all or part of said genome of the parent virus, (ii) a second DNA fragment comprising a first portion of said exogenous DNA sequence equipped at its 5' end with said flanking sequence A and (iii) a third DNA fragment comprising a second portion of said exogenous DNA sequence equipped at its 3' end with said flanking sequence B; said second and third DNA fragments containing a homologous sequence overlapping at their respective 3' and 5' ends. As a guide, these sequences which are homologous between the second and third DNA fragments satisfy the same criteria of homology and of length as the sequences A and B. This specific embodiment is especially advantageous for the cloning of large-sized exogenous sequences.

A method according to the invention may be carried out in any prokaryotic cell, and in particular in a bacterium derived from an *Escherichia coli* strain. However, it is most especially preferable to employ a recBC sbcBC strain such as, for example, the strains CES200, CES201, W5449 and BJ5183 (Hanahan, 1983, J. Mol. Biol., 166, 557–580).

A procedure typical of a method according to the invention comprises the following steps:
(a) a first DNA fragment and (ii) a second DNA fragment, as are defined above, are cointroduced or introduced separately into a prokaryotic cell,
(b) the prokaryotic cell obtained in step (a) is cultured under suitable conditions to permit the generation of the recombinant viral vector by intermolecular recombination, and
(c) the recombinant viral vector is recovered.

In the context of a method according to the invention, the amounts of first and second DNA fragments may vary. It is preferable to employ a concentration of second fragment which is 10 times as large as that of the first fragment. The introduction of the DNA fragments into a prokaryotic cell and the recovery of the vector from these same cells are carried out according to the general techniques of genetic engineering and of molecular cloning detailed in Maniatis et al. (1989, Laboratory Manual, Cold Spring Harbor, Laboratory Press, Cold Spring Harbor, N.Y.).

The present invention also relates to a method for preparing an infectious viral particle containing a recombinant viral vector obtained by carrying out a method according to the invention, according to which:
(a) said recombinant viral vector is introduced into a mammalian cell to generate a transfected mammalian cell,
(b) said transfected mammalian cell is cultured under suitable conditions to permit the production of said viral particle, and
(c) said viral particle is recovered from the cell culture obtained in step (b).

The cells may be transfected according to the standard techniques well known to a person skilled in the art. The calcium phosphate technique, the DEAE-dextran technique, electroporation, methods based on osmotic shock, microinjection or methods based on the use of liposomes may be mentioned in particular. According to a preferred embodiment, the mammalian cell is advantageously a complementation cell, and in particular the 293 cell in the context of a vector derived from an adenovirus. The viral particles may be recovered from the culture supernatant, but also from the cells according to conventional protocols.

The present invention also covers the use of an infectious viral particle or of a recombinant viral vector prepared according to a method according to the invention, for the therapeutic or surgical treatment of the human body, and in particular by gene therapy. A method according to the invention is intended more especially for the preventive or curative treatment of diseases such as genetic diseases (hemophilia; thalassemias, emphysema, Gaucher's disease, cystic fibrosis, Duchenne's or Becker's myopathy, etc.), cancers and viral diseases (AIDS, herpes infections or infections caused by cytomegalovirus or by papillomavirus). For the purposes of the present invention, the vectors and viral particles prepared by a method according to the invention may be introduced either in vitro into a host cell removed from the patient, or directly in vivo into the body to be treated. Preferably, the host cell is a human cell, and preferably a lung, fibroblast, muscle, liver or lymphocytic cell or a cell of the hematopoietic line.

The present invention also relates to a pharmaceutical composition comprising a therapeutically effective amount of an infectious viral particle or of a recombinant viral vector prepared according to a method according to the invention, in combination with a vehicle which is acceptable from a pharmaceutical standpoint. Such a pharmaceutical composition may be prepared according to the techniques commonly employed and administered by any known administration route, for example systemically (in particular intravenously, intratracheally, intraperitoneally, intramuscularly, subcutaneously, intratumorally or intracranially) or by aerosolization or intrapulmonary instillation.

Lastly, the subject of the present invention is also the use of an infectious viral particle or of a recombinant viral vector prepared according to a method according to the invention, for the expression of a DNA sequence of interest in a cell system.

The present invention is described more completely by reference to the figures which follow and by means of the examples which follow.

BRIEF DESCRIPTION OF THE INVENTION

EXAMPLES

The examples which follow illustrate just one embodiment of the present invention.

The constructions described below are carried out according to the general techniques of genetic engineering and molecular biology detailed in Maniatis et al. (1989, supra). 5' protruding restriction sites may be converted to blunt sites by treatment with the large Klenow fragment of E. coli DNA polymerase, whereas 3' protruding sites are treated with T4 polymerase. As regards the steps of PCR amplification, the protocol as described in PCR Protocols—A guide to methods and applications (1990, ed. Innis, Gelfand, Sninsky and White, Academic Press Inc.) is applied. Cells are transfected by conventional methods and are cultured according to the supplier's recommendations. The fragments inserted into the different constructions described below are indicated precisely according to their position in the Ad5 genome as disclosed in the Genebank databank under the reference M73260.

EXAMPLE 1

Construction of a Recombinant Viral Vector Derived From a Tope 5 Human Adenovirus in the Form of a Bacterial Plasmid A. Cloning of the adenovirus 5 (Ad5) genome into p polyII The left-hand end of the Ad5 genome (nucleotides 1 to 935) is synthesized by PCR using the oligonucleotide primers oTG6597 (SEQ ID NO: 1) and oTG6598 (SEQ ID NO: 2). The first primer hybridizes with the first 21 nucleotides of the 5' ITR, and possesses a PacI site immediately upstream of the viral sequences and an EcoRI site used for the cloning. The second primer enables SalI and then BglII sites to be introduced downstream of the viral sequences. The template utilized in this reaction is Ad5 genomic DNA prepared according to conventional methods. The fragment thus amplified is digested with EcoRI and BglII [sic] and cloned into the plasmid p polyII (Lathe et al., 1987, supra) previously cleaved with these same two restriction enzymes, to give pTG1692.

The DNA fragment corresponding to the right-hand end of the Ad5 genome (nucleotides 35103 to 35935) is prepared according to the same principle, using the oligonucleotide pair oTG6599 (SEQ ID NO: 3) and oTG6597 (SEQ ID NO: 1). pTG1693 is constructed by inserting the amplified fragment, digested with EcoRI and BglII, into the same sites of p polyII. A BglII-BamHI fragment carrying the amplified sequences is excised from pTG1693 so as to introduce it into the BglII site of pTG1692 downstream of the adenoviral 5' sequences. pTG3601 thereby obtained is linearized between the left-hand and right-hand ends of the Ad5 genome by digestion with restriction enzymes BglII or SalI. The ends thus generated are blunted by the action of the Klenow fragment of E. coli DNA polymerase I. BJ5183 bacteria (Hanahan, 1983 supra), made competent by calcium chloride treatment, are cotransformed with the above preparation and the Ad5 genomic DNA. The colonies obtained are analyzed by restriction mapping. One clone is selected, designated pTG3602, generated by intermolecular homologous recombination, in which the adenoviral sequences (nucleotides 936 to 35102) have been inserted between the two fragments produced by PCR, so as to generate a plasmid vector comprising the complete Ad5 genome-pTG3602 is produced in C600 bacteria (Huynh et al., 1985 DNA cloning, Volume 1, ed. Glover, IRL Press Limited: Oxford, England pp. 56110).

B. Evaluation of the infectious power of pTG3602

The viral genome is liberated by the action of the restriction enzyme PacI. 293 cells cultured in a monolayer are transfected with the product of this digestion by the calcium phosphate precipitation technique. It is also possible to use other sensitive cells, for example A549 cells (ATCC CCL185). The cells are grown under agar for 9 to 14 days, during which period the appearance of lytic plaques on the cell lawn testifies to the production of infectious viral particles, and hence to the capacity of the Ad5 genome originating from pTG3602 to replicate.

C. Construction of a defective recombinant adenoviral vector in which the exogenous gene replaces the E1 early region.

A plasmid is used in which the LacZ reporter gene coding for β-galactosidase is placed in a viral context; for example a plasmid derived from pMLP-Adk7 (Stratford-Perricaudet and Perricaudet, 1991, Human Gene Transfer, 219, 51–61) comprising the Ad5 5' sequences (nucleotides 1 to 458), the Ad2 MLP promoter, the LacZ gene, the SV40 virus polyadenylation signal and the Ad5 sequences lying between nucleotides 3329 and 6241.

The LacZ gene expression cassette surrounded by adenoviral sequences is excised by the action of the restriction enzymes BsrGI (position 192 on the Ad5 genome) and PstI (position 3788) and then purified. pTG3602 is linearized at the ClaI site (position 918) and then treated with Klenow. The two fragments obtained are cotransformed into competent BJ5183 bacteria. Recombination at the homologous adenoviral sequences brings about the replacement of the Ad5 E1 region (nucleotides 459 to 3328) by the expression cassette for the reporter gene in the plasmid pTG3603.

Its infectious power is verified by transfection of a lawn of 293 cells transfected with pTG3603 previously digested with PacI. The lytic plaques formed are then picked out and the viral particles resuspended and used to infect a monolayer of 293 cells. The blue coloration of the cells after addition of X-Gal testifies to the expression of the LacZ gene.

D. Construction of a recombinant adenoviral vector in which the exogenous gene replaces the E3 early region.

A cassette for the expression of the gene coding for the gp19 protein of the Ad5 E3 region (nucleotides 28731 to 29217) is assembled in the bacteriophage M13mp18 (Gibco BRL) by cloning two PCR fragments, one corresponding to the RSV (Rous sarcoma virus) 3' LTR (oligonucleotide primers oTG5892-SEQ ID NO: 4 and 5893-SEQ ID NO:5) and the other to the sequence coding for gp19 (oTG5455-SEQ ID NO:6 and 5456-SEQ ID NO:7). The vector M13TG1683 is obtained, from which the expression cassette is excised by an XbaI digestion. After treatment with Klenow, it is introduced into the BsmI site (blunted by the action of phage T4 DNA polymerase) of pTG8519. The latter is derived from the plasmid puc19 (Gibco BRL), into which the adenoviral sequences lying between the SpeI site and the right-hand end of the genome (nucleotides 27082 to 35935) but lacking the majority of the E3 region (nucleotides 27871 to 30758) have been inserted. pTG1695 is obtained, the ScaI-SpeI fragment of which, carrying the plasmid sequences, is replaced by a purified equivalent fragment of pTG1659. The latter corresponds to puc19 [sic] comprising the Ad5 sequences extending from nucleotides 21562 to 35826. pTG1697 thereby obtained possesses adenoviral sequences which extend from the BamHI (position 21562) site to the 3' ITR (position 35935), in which sequences the E3 region is replaced by a gp19 expression cassette under the control of the RSV constitutive promoter. the DraI fragment (position 22444 and 35142 on the Ad5 genome) is purified, and cointroduced into competent BJ-5183 bacteria with pTG3602 linearized with SpeI and treated with Klenow. The recombinants carrying a plasmid generated by recombination are screened for the presence of the RSV promoter. pTG3605, a plasmid vector carrying the Ad-gp19+genome, is thus demonstrated.

The infectious power viral genome excised from plasmid pTG3605 is tested according to the protocol already described above. The production of a functional gp19 protein is monitored by co-immunoprecipitation of the antigens of the major histocompatibility complex class I and of the protein (Burgert and Kvist, 1985, Cell, 41, 987–997).

E. Construction of a defective recombinant adenoviral vector in which both early regions E1 and E3 are replaced by exogenous genes BJ-5183 cells are cotransformed with the DraI fragment isolated from pTG1697 mentioned above, and the SpeI fragment (Klenow) isolated from pTG3603. The resulting plasmid is tested under the same conditions as above.

F. Construction of a recombinant adenoviral vector expressing the FIX gene

The cDNA coding for human FIX was cloned in the form of a BamHI fragment into the plasmid pTG381. In the latter, the 5' non-coding end of the FIX gene was modified so as to comply with Kozak's rules. Plasmid pTG381 is described in Patent Publication FR 2,600,334. The FIX gene is recloned into the BamHI site of pTG6512 to give pTG4375. pTG6512 is derived from the vector pTG6511 after deletion of the Ad2 major late promoter (MLP) and replacement by a polylinker. As a guide, the construction of pTG6511 is described in detail in Example 1 of International Application WO 94/28152. The murine PGK promoter is isolated by conventional methods from mouse genomic DNA according to Adra et al. (1987, Gene 60, 65–74), or by means of appropriate primers created from the data of the sequence disclosed in the Genebank databank under the reference X15339. PstI restriction sites are included at the 5' ends of the primers in order to facilitate the subsequent cloning steps. The fragment carrying the PGK promoter is treated with T4 polymerase and then introduced upstream of the human FIX gene into the HpaI site of pTG4375 from which a so-called "replacement" fragment, containing the FIX cassette surrounded by E1 adenoviral sequences (185 bp at the 5' end and 2045 bp at the 3' end), is excised by MscI digestion.

Figure 3:
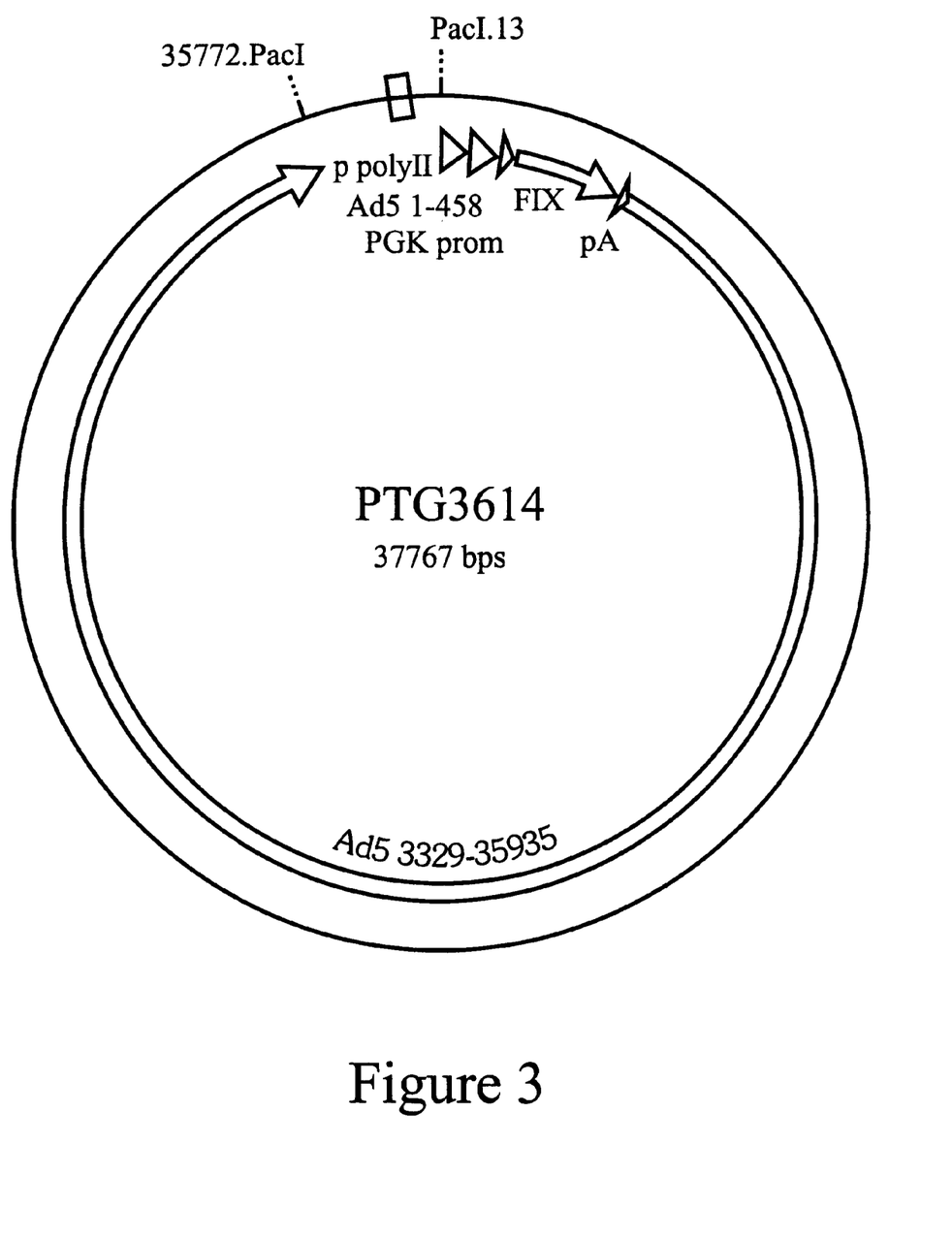
FIG. 3 is a diagrammatic representation of the vector pTG3614, corresponding to p polyII into which is cloned the genome of a recombinant adenovirus modified in the E1 region by insertion of a cassette for the expression of the human FIX gene.

The latter fragment is cotransformed into BJ5183 bacteria in the presence of the vector pTG3602 digested with ClaI (position 918). The transformants are selected on ampicillin and analyzed by restriction mapping. The clone designated pTG3614, corresponding to an adenoviral vector containing the FIX therapeutic gene in place of the E1 region (FIG. 3), is selected. A viral stock is constituted in a conventional manner, by transfection of the adenoviral genome liberated by PacI digestion into the 293 line. After an amplification step, the cells are lysed and the AdTG3614 viral particles purified by centrifugation on cesium chloride.

The capacity to transfer and express the FIX gene is evaluated in a mouse animal model. For this purpose, $1.5 \times 10^9$ pfu are injected into the caudal vein of 5- to 6-week-old female C57 Black 6 mice. Blood samples are drawn regularly, on which the amount of human FIX is assayed by ELISA (Diagnostica Stago Kit, Asnieres, France; AsserachiromR IX: Ag 00564). FIX is detected in the serum of mice for several weeks with a maximum at 5 days.

G. Construction of an adenoviral vector modified in the E2 region

During the normal viral cycle, the expression of the genes of the E2 region is induced by the early products of E1 and E4, and a copious production of the proteins encoded by E2, and especially of the DBP protein (for DNA binding protein), is observed. In point of fact, this high expression can be problematical in vivo (induction of inflammatory responses or interference with the expression of the transgene). For this reason, adenoviral vectors defective for the E2A function were constructed, either by introduction of a temperature-sensitive mutation into E2A (position 22795; C to T resulting in a change from Pro to Ser) or by a partial deletion of the DBP gene.

The vector pTG9551 carrying the temperature-sensitive mutation is generated by homologous recombination in BJ cells between pTG3601 digested with BglII and the purified genomic DNA of the Ad5Hts 125 virus (Ensinger and Ginsberg, 1972, J. Virol. 10, 328–339). The genome thus reconstituted is liberated by PacI digestion and transfected into 293 cells, which are incubated at 32° C. for the production of the viral particles (the non-permissive temperature is 39° C.).

The defective E2A character may also be generated by partial deletion of the coding regions of the DBP gene, avoiding the regions covering other reading frames. The construction is carried out by homologous recombination between pTG3601 BglII and the viral DNA prepared from the H5d1802 virus (Rice and Klessig, 1985, J. Virol. 56, 767–778). The viruses may be produced in a suitable complementation line transcomplementing the DBP function, for example line 293 transfected with a vector permitting the constitutive or regulated expression of the DBP gene.

H. Construction of an adenoviral vector modified in the E4 region

In a first stage, a so-called "replacement" vector is constructed, comprising a cassette for the expression of the gene coding for the CFTR protein placed within the E1 adenoviral region. This vector, designated pTG8585, contains the following elements, all described in the literature:

the Ad5 5' ITR (positions 1 to 458), the Ad2 MLP promoter, human CFTR cDNA, the polyadenylation signal of the rabbit β-globin gene, the RSV virus (Rous sarcoma virus) 3' LTR, the adenoviral sequences coding for the gp19 protein (positions 28731 to 29217 of Add5), and the 3' portion of the E1B region (position 3329 to 6241).

In parallel, the adenoviral sequences covering the E3 and E4 regions are subcloned into the vector p polyII and deleted by the standard techniques of molecular biology. The E3 sequences (positions 28592 to 30470) are removed by XbaI digestion and the E4 sequences (positions 32994 to 34998) are removed. The adenoviral genome thus modified is reconstituted by homologous recombination between a replacement fragment carrying these modifications, isolated from the above vector, and pTG3603 digested with SpeI. pTG8595 is obtained, carrying a recombinant adenoviral genome (LacZ gene in place of the E1 region) which is defective for the E3 and E4 functions.

Figure 4:
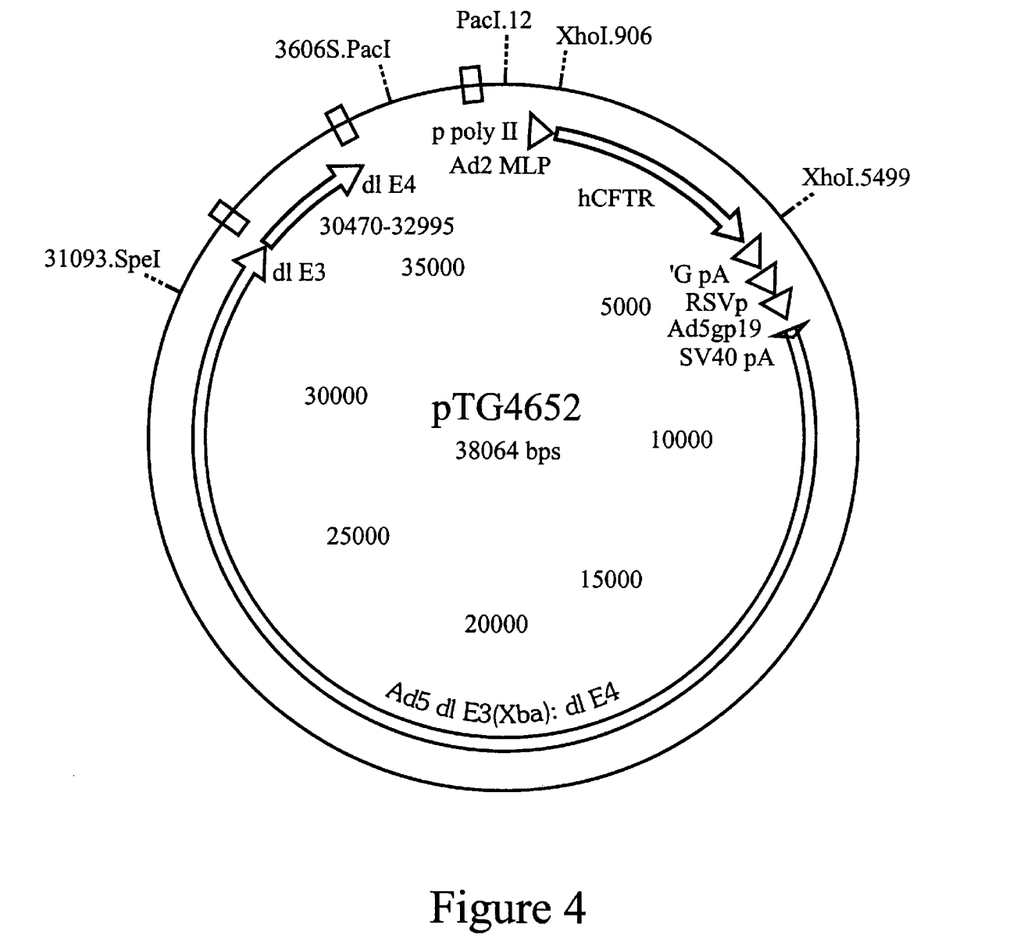
FIG. 4 is a diagrammatic representation of the vector pTG4652, corresponding to p polyII into which is cloned the genome of a recombinant adenovirus modified in the E1, E3 and E4 regions by insertion of a cassette for the expression of the human CF gene and partial deletions.

The cassettes for the expression of the CFTR and gp19 genes, described above, are introduced into pTG8595 as a replacement for the LacZ gene, by cotransformation of BJ5183 cells with the PacI-BstEII fragment isolated from pTG8585 and the vector pTG8595 linearized with ClaI. pTG4652 (FIG. 4) is generated, which may be propagated in a cell line complementing the defective E1 and E4 functions as are described in International Application WO94/28152.

The viral particles are amplified, the cells are lysed and the total cell extracts are analyzed for the expression of the CFTR gene by Western blotting (8% SDSPAGE gel). The filters are incubated in the presence of a 1/5000 dilution of the monoclonal antibody MAB 1104 directed against a synthetic peptide corresponding to amino acids 722 to 734 of the human CFTR protein. The detection is carried out by the ECL (enhanced chemiluminescence; Amersham kit) method. A band of strong intensity and rather diffuse, corresponding to a high molecular weight product comigrating with a CFTR control, is observed in the extracts of cells infected with AdTG4652. This band is not present in the extracts originating from the parent virus pTG8595 which does not contain the CFTR expression cassette.

EXAMPLE 2

Construction of a Recombinant Viral Vector Derived From Canine Adenovirus 2 (CAV2) in the Form of a Bacterial Plasmid A. Cloning of the CAV2 genome into p polyII The CAV2 genome is cloned into p polyII SfiI-NotI 14 (Lathe et al., 1987, supra) and modified to generate recombinant vectors using the appropriate sites, according to the same methods as are used in the case of the manipulation of Ad5. The left-hand end (nucleotides 1 to 810 according to the numbering of the Genebank sequence D04368) and right-hand end (nucleotides~27600 to the end) are synthesized by PCR between the oligois nucleotide primer pairs oTG6974 (SEQ ID NO: 8) and oTG6975 (SEQ ID NO: 9) and oTG6976 (SEQ ID NO: 10) and oTG6974, respectively. They are assembled via the PstI site introduced during the PCR following the viral sequences in the case of the left-hand end, and mapped at approximately 1200 bp from the end of the genome in the case of the right-hand end. Competent BJ5183 bacteria are cotransformed with the plasmid thereby obtained, linearized with PstI, and CAV2 DNA. Introduction of the missing viral sequences (nucleotides 811 to 27600) is carried out by homologous recombination. The CAV2 genome carried by the resulting plasmid is excised via the NotI sites introduced during the PCR, and then transfected into a monolayer of MDCK cells (ATCC CCL34). The following steps are described in Example 1.

B. Construction of a recombinant adenoviral vector of canine origin

CAV2 virus (strain Toronto A 26/61; ATCC VR-800) genomic DNA is prepared by the standard technique (amplification on a dog kidney line MDCK GHK, etc., lysis of the cells, purification of the viruses by centrifugation on cesium chloride, treatment with proteinase k and lastly phenol/chloroform extraction). The CAV2 genome, which is 31 kbp in length, is introduced into a plasmid vector by homologous recombination. For this purpose, the left-hand and right-hand ends of the CAV2 genome are isolated by PCR and enzymatic digestion, incorporating a NotI site immediately beyond the 5' and 3' ITRs. The vector pTG4457 is obtained by introducing into p polyII the 5' portion of the viral genome as far as the BstBI site (position 870) followed by the 3' portion starting from the SalI site (position 27800). The complete genome may be reconstituted by cotransformation between the genomic DNA (100 to 500 ng) and pTG4457 digested with BstBI (10 to 100 ng). The viral genome may be excised from the above vector pTG5406 by NotI digestion. It is verified that the DNA is infectious by transfection of 1 to 5 μg into dog MDCK or GHK cells. The production of plaques is observed.

The recombinant vector is obtained in the following manner:

The left-hand end of CAV2 is subcloned and modified so as to delete the E1A coding sequences in their entirety and the E1B coding sequences partially. This is performed by NarI digestion, followed by reintroduction of a fragment amplified by PCR covering the encapsidation region, the E1A promoter region and the transcription startsite. The primers are designed so as to integrate a unique XbaI restriction site as well. pTG5407 is obtained, into which the CAT gene or LacZ gene (pTG5408) is introduced at the XbaI site. The latter plasmid is digested with XhoI, and the 3' portion of the viral genome is inserted in the form of a SalI fragment (position 27800 to the end of the 3' ITR). The vector pTG5409 thereby obtained is linearized with SalI and cotransformed into *E. coli* BJ5183 with the CAV-2 genome digested with SwaI. An adenoviral vector of canine origin carrying the CAT reporter gene in place of the El region is obtained.

What is claimed is:

1. A method for preparing, in a prokaryotic cell, a recombinant adenoviral vector into the genome of which an exogenous DNA sequence is inserted, by intermolecular homologous recombination comprising the steps of
   (a) introducing into said prokaryotic cell:
      (i) a first DNA fragment comprising all of said genome of the adenovirus or said adenoviral genome lacking all or part of the E1 region, E2 region, E3 region, E4 region or a combination thereof, and
      (ii) a second DNA fragment comprising said exogenous DNA sequence surrounded by flanking sequences A and B which are homologous to sequences of (i) not including sequences of the 5'ITR, 3'ITR and encapsidation regions of said adenoviral genome, such as to allow intermolecular homologous recombination; wherein the first and second DNA fragments are not carried by a single vector, and
   (b) culturing the prokaryotic cell obtained in (a) under suitable culture conditions to allow homologous recombination and insertion of the exogenous DNA into the first DNA fragment to occur, and recovering the resulting recombinant adenoviral vector.

2. The method according to claim 1, wherein the adenovirus is of human, canine, avian, bovine, murine, ovine, porcine, or simian origin, or said adenovirus is a hybrid adenovirus.

3. The method according to claim 2, wherein the adenovirus is a type CAV-2 adenovirus of canine origin.

4. The method according to claim 2, wherein the adenovirus is a serotype C adenovirus of human origin.

5. The method according to claim 4, wherein the adenovirus is a type 5 adenovirus of human origin.

6. The method according to claim 1, wherein said exogenous DNA sequence codes for a polypeptide of therapeutic interest selected from the group consisting of coagulation factors, growth hormones, cytokines, lymphokines, tumor-suppressing polypeptides, cell receptors, ligands for cell receptors, protease inhibitors, antibodies, toxins, immunotoxins, dystrophin and polypeptides participating in cellular ion channels.

7. The method according to claim 1, wherein the homologous flanking sequences A and B are from 10 consecutive bp to 10 consecutive kb in length.

8. The method according to claims 1, wherein the first DNA fragment is linearized in the region where said exogenous sequence is inserted.

9. The method according to claim 1, wherein said first DNA fragment lacks all or part of at least one region essential for replication, selected from the group consisting of the E1, E2, E3 and E4 regions and wherein the recombinant adenoviral vector is defective for replication.

10. The method according to claim 9, wherein the recombinant adenoviral vector lacks all or part of the E3 region.

11. The method according to claim 1, wherein the recombinant adenoviral vector is of at least 20 kb.

12. The method according to claim 11, wherein the recombinant adenoviral vector is of at least 30 kb.

13. A method for preparing, in a prokaryotic cell, a recombinant adenoviral vector into the genome of which an exogenous DNA sequence is inserted by intermolecular homologous recombination comprising the steps of
   (a) introducing into said prokaryotic cell:
      (i) a first DNA fragment comprising all of said genome of the adenovirus or said adenoviral genome lacking all or part of the E1 region, E2 region, E3 region, E4 region or a combination thereof,
      (ii) a second DNA fragment comprising a first portion of said exogenous DNA sequence whose 5' end is equipped with a flanking sequence A, and
      (iii) a third DNA fragment comprising a second portion of said exogenous DNA sequence whose 3' end is equipped with a flanking sequence B; said second and third DNA fragments further containing an overlapping homologous sequence at their respective 3' and 5' ends, and said flanking sequences A and B being homologous to sequences of (i) not including sequences of the 5'ITR, 3'ITR, and encapsidation regions of said adenoviral genome, such as to allow for intermolecular homologous recombination, and
   (b) culturing the prokaryotic cell obtained in (a) under suitable culture conditions to allow homologous recombination to occur, and recovering the resulting recombinant adenoviral vector.

14. The method according to claim 1, wherein said prokaryotic cell is a recBC sbcBC strain of *Escherichia coli*.

15. A method for preparing an adenoviral particle containing a recombinant adenoviral vector, according to which:
   (a) a recombinant adenoviral vector obtained according to method of claim 1 is introduced into a mammalian cell to generate a transfected mammalian cell,
   (b) said transfected mammalian cell is cultured under suitable conditions to permit the production of said adenoviral particle, and
   (c) said adenoviral particle is recovered from the cell culture obtained in step (b).

16. A method for preparing in a prokaryotic cell, a recombinant adenoviral vector into the genome of which an exogenous DNA sequence is inserted by intermolecular homologous recombination comprising the steps of:
   (i) preparing a first DNA fragment comprising all of said adenoviral genome or said adenoviral genome lacking all or part of the E1 region, E2 region, E3 region, E4 region or any combination thereof, said first DNA fragment being linearized in a region where insertion of said exogenous DNA sequence is targeted,
   (ii) preparing a linear second DNA fragment comprising said exogenous DNA sequence and flanking sequences A and B located at both sides of said linear second DNA fragment, and said flanking sequences A and B being homologous to sequences of (i) not including sequences of the 5'ITR, 3'ITR and encapsidation regions of said adenoviral genome, such as to allow for intermolecular homologous recombination, (iii) introducing said first DNA fragment and second DNA fragment into said prokaryotic cell, (iv) culturing the prokaryotic cell obtained in step (iii) under suitable culture conditions, and (v) recovering the recombinant adenoviral vector.

17. A method for modifying in a prokaryotic cell, a particular region of an adenoviral vector genome by intermolecular homologous recombination comprising the steps of (a) introducing into said prokaryotic cell:

(i) a first DNA fragment comprising all of said adenoviral vector genome or said adenoviral vector genome lacking all or part of the E1 region, E2 region, E3 region, E4 region or a combination thereof and (ii) a second DNA fragment comprising said particular adenoviral region of which one or more nucleotides is modified by introduction of a deletion, addition, substitution, or any combination thereof, surrounded by flanking sequences A and B which are homologous to sequences of (i) not including sequences of the 5'ITR, 3'ITR and encapsidation regions of said adenoviral genome, such as to allow for intermolecular homologous recombination, wherein the first and second DNA fragments are not carried by a single vector, and (b) culturing the prokaryotic cell obtained in (a) under suitable culture conditions to allow homologous recombination to occur, and recovering the resulting recombinant adenoviral vector.

18. A method for modifying in a prokaryotic cell, a particular region of an adenoviral vector genome by intermolecular homologous recombination comprising the steps of:

(i) preparing a first DNA fragment comprising all of said adenoviral vector genome or said adenoviral vector genome lacking all or part of the E1 region, E2 region, E3 region, E4 region or a combination thereof, said first DNA fragment being linearized in said particular region, (ii) preparing a linear second DNA fragment comprising said particular region flanked by sequences A and B located at both sides of said linear second DNA fragment, wherein said particular region is modified by introduction of a deletion, addition, substitution, or any combination thereof, of one or more nucleotides and said flanking sequences A and B are homologous to sequences of (i) not including sequences of the 5'ITR, 3'ITR and encapsidation regions of said adenoviral genome, such as to allow for intermolecular homologous recombination, (iii) introducing said first DNA fragment and second DNA fragment into said prokaryotic cell, (iv) culturing the prokaryotic cell obtained in step (iii) under suitable culture conditions, and (v) recovering the modified adenoviral vector.

* * * * *

SEQUENCE LISTING

<160> NUMBER OF SEQ ID NOS: 10

<210> SEQ ID NO 1
<211> LENGTH: 38
<212> TYPE: DNA
<213> ORGANISM: human adenovirus

<400> SEQUENCE: 1
gccgaattct taattaacat catcaataat atacctta                                38

<210> SEQ ID NO 2
<211> LENGTH: 35
<212> TYPE: DNA
<213> ORGANISM: human adenovirus

<400> SEQUENCE: 2

-continued

```
gacagatctg tcgacgtggc aggtaagatc gatca                    35

<210> SEQ ID NO 3
<211> LENGTH: 35
<212> TYPE: DNA
<213> ORGANISM: human adenovirus

<400> SEQUENCE: 3
aggagatctg tcgactctca aacatgtctg cgggt                    35

<210> SEQ ID NO 4
<211> LENGTH: 47
<212> TYPE: DNA
<213> ORGANISM: rous sarcoma virus

<400> SEQUENCE: 4
gtcgtaggat ccagctgctc cctgcttgtg tgttggaggt cgctgag       47

<210> SEQ ID NO 5
<211> LENGTH: 47
<212> TYPE: DNA
<213> ORGANISM: rous sarcoma virus

<400> SEQUENCE: 5
gtagctgacg tcccaggtgc acaccaatgt ggtgaatggt caaatgg       47

<210> SEQ ID NO 6
<211> LENGTH: 25
<212> TYPE: DNA
<213> ORGANISM: human adenovirus

<400> SEQUENCE: 6
atcggaattc aagatgatta ggtac                               25

<210> SEQ ID NO 7
<211> LENGTH: 28
<212> TYPE: DNA
<213> ORGANISM: human adenovirus

<400> SEQUENCE: 7
atcgtctaga ttaaggcatt ttcttttc                            28

<210> SEQ ID NO 8
<211> LENGTH: 36
<212> TYPE: DNA
<213> ORGANISM: canine adenovirus

<400> SEQUENCE: 8
cagggatccg cggccgcatc atcaataata tacagg                   36

<210> SEQ ID NO 9
<211> LENGTH: 29
<212> TYPE: DNA
<213> ORGANISM: canine adenovirus

<400> SEQUENCE: 9
ctgctgcagt cagaaatgct agcaggaga                           29

<210> SEQ ID NO 10
```

-continued

```
<211> LENGTH: 27
<212> TYPE: DNA
<213> ORGANISM: canine adenovirus

<400> SEQUENCE: 10
tgcggatcca cagactaagc ggaggta                                              27
```